United States Patent
Alesi et al.

(10) Patent No.: US 10,993,764 B1
(45) Date of Patent: May 4, 2021

(54) INSULATING GRIPS FOR MINIMALLY INVASIVE SURGICAL INSTRUMENTS

(71) Applicant: Microline Surgical, Inc., Beverly, MA (US)

(72) Inventors: Christopher Alesi, Saugus, MA (US); Dennis Pelletier, Byfield, MA (US)

(73) Assignee: Microline Surgical, Inc., Beverly, MA (US)

(*) Notice: Subject to any disclaimer, the term of this patent is extended or adjusted under 35 U.S.C. 154(b) by 0 days.

(21) Appl. No.: 17/099,415

(22) Filed: Nov. 16, 2020

Related U.S. Application Data

(60) Provisional application No. 62/961,012, filed on Jan. 14, 2020.

(51) Int. Cl.
*A61B 18/14* (2006.01)
*A61B 17/29* (2006.01)
(Continued)

(52) U.S. Cl.
CPC ...... *A61B 18/1445* (2013.01); *A61B 17/3201* (2013.01); *A61B 17/32053* (2013.01);
(Continued)

(58) Field of Classification Search
CPC ............ A61B 18/1445; A61B 17/0467; A61B 17/0469; A61B 18/1442; A61B 10/02;
(Continued)

(56) References Cited

U.S. PATENT DOCUMENTS

| | | |
|---|---|---|
| 5,171,247 A | 12/1992 | Hughett et al. |
| 5,171,249 A | 12/1992 | Stefanchik et al. |

(Continued)

FOREIGN PATENT DOCUMENTS

| | | |
|---|---|---|
| CA | 3029763 | 3/2018 |
| EP | 0712608 A2 | 5/1996 |

(Continued)

OTHER PUBLICATIONS

PCT/US2020/061837, International Search Report and Written Opinion, dated Mar. 4, 2021, 13 pages.

*Primary Examiner* — Nathaniel C Chukwurah
(74) *Attorney, Agent, or Firm* — Kilpatrick Townsend & Stockton LLP

(57) ABSTRACT

A surgical instrument with insulating grips is described. The grips can include internal metal frames that are arranged to limit electrical conductivity within the grips and to other components that attach to a grip, such as a ratchet. The internal metal frames can be constructed of multiple internal portions, spatially separated from one another to interrupt electrical conductivity between the internal portions, but coated with an insulating overmold to provide mechanical coupling between the portions. An internal metal frame can also include a notch, cut-out, or other region partially surrounded by the structure of the internal metal frame, which can be coated with an insulating overmold to define a region of the grip that does not have an internal metal frame therein but which can include an attachment point for mechanically coupling other components while limiting electrical coupling between the metal frame and the other components.

20 Claims, 4 Drawing Sheets

(51) Int. Cl.
    *A61B 18/00*     (2006.01)
    *A61B 17/00*     (2006.01)
    *A61B 17/3201*     (2006.01)
    *A61B 17/32*     (2006.01)
    *A61B 17/3205*     (2006.01)

(52) U.S. Cl.
    CPC ............ *A61B 2017/00407* (2013.01); *A61B 2017/00473* (2013.01); *A61B 2017/00526* (2013.01); *A61B 2017/00955* (2013.01); *A61B 2017/2925* (2013.01); *A61B 2017/320044* (2013.01); *A61B 2018/00083* (2013.01); *A61B 2018/00178* (2013.01); *A61B 2018/00595* (2013.01)

(58) Field of Classification Search
    CPC ........ A61B 2018/1253; A61B 17/3201; A61B 2017/2931; A61B 17/320016
    See application file for complete search history.

(56) References Cited

U.S. PATENT DOCUMENTS

| | | | |
|---|---|---|---|
| 5,275,612 A | 1/1994 | Bales, Jr. | |
| 5,483,952 A | 1/1996 | Aranyi | |
| 5,578,052 A | 11/1996 | Koros et al. | |
| 5,611,813 A * | 3/1997 | Lichtman | A61B 17/29 606/174 |
| RE35,525 E | 6/1997 | Stefanchik et al. | |
| 5,769,849 A | 6/1998 | Eggers | |
| 5,792,165 A * | 8/1998 | Klieman | A61B 17/29 606/170 |
| 5,827,323 A * | 10/1998 | Klieman | A61B 17/29 606/205 |
| 5,846,240 A | 12/1998 | Kortenbach et al. | |
| 6,325,795 B1 | 12/2001 | Lindemann et al. | |
| 6,402,747 B1 | 6/2002 | Lindemann et al. | |
| 6,432,115 B1 | 8/2002 | Mollenauer et al. | |
| 6,595,984 B1 | 7/2003 | DeGuillebon | |
| 6,866,672 B2 | 3/2005 | Mollenauer et al. | |
| 7,011,656 B2 | 3/2006 | Mcgaffigan et al. | |
| 7,025,065 B2 | 4/2006 | Mcgaffigan et al. | |
| 7,103,947 B2 | 9/2006 | Sartor et al. | |
| 7,261,724 B2 | 8/2007 | Molitor et al. | |
| 7,288,098 B2 | 10/2007 | Huitema et al. | |
| 7,297,149 B2 | 11/2007 | Vitali et al. | |
| 7,419,495 B2 | 9/2008 | Menn et al. | |
| 7,686,820 B2 | 3/2010 | Huitema et al. | |
| 7,731,724 B2 | 6/2010 | Huitema et al. | |
| 7,740,641 B2 | 6/2010 | Huitema | |
| 8,038,686 B2 | 10/2011 | Huitema et al. | |
| 8,075,571 B2 | 12/2011 | Vitali et al. | |
| 8,216,257 B2 | 7/2012 | Huitema et al. | |
| 8,236,012 B2 | 8/2012 | Molitor et al. | |
| 8,246,615 B2 | 8/2012 | Behnke | |
| 8,246,634 B2 | 8/2012 | Huitema et al. | |
| 8,246,635 B2 | 8/2012 | Huitema | |
| 8,328,822 B2 | 12/2012 | Huitema et al. | |
| 8,355,803 B2 | 1/2013 | Bonn et al. | |
| 8,523,882 B2 | 9/2013 | Huitema et al. | |
| 8,753,356 B2 | 6/2014 | Vitali et al. | |
| 8,821,516 B2 | 9/2014 | Huitema | |
| 8,915,930 B2 | 12/2014 | Huitema et al. | |
| 9,370,343 B2 | 6/2016 | Ryll et al. | |
| 9,480,466 B2 | 11/2016 | Van De Weghe et al. | |
| 9,561,076 B2 | 2/2017 | Brannan et al. | |
| 9,717,504 B2 | 8/2017 | Huitema | |
| 9,750,500 B2 | 9/2017 | Malkowski | |
| 9,782,181 B2 | 10/2017 | Vitali et al. | |
| 9,814,515 B2 | 11/2017 | Mcgaffigan et al. | |
| 10,159,491 B2 | 12/2018 | Gokharu | |
| 10,363,045 B2 | 7/2019 | Whitfield et al. | |
| 10,405,862 B2 | 9/2019 | Patel et al. | |
| 10,729,450 B2 | 8/2020 | Chang et al. | |
| 10,837,329 B2 | 11/2020 | Parrish et al. | |
| 2008/0015575 A1 | 1/2008 | Odom et al. | |
| 2010/0179545 A1* | 7/2010 | Twomey | A61B 18/1445 606/51 |
| 2011/0306952 A1 | 12/2011 | Chen et al. | |
| 2015/0173825 A1 | 6/2015 | Bloom | |
| 2016/0287320 A1 | 10/2016 | Hiller | |
| 2017/0273689 A1 | 9/2017 | Huitema | |
| 2017/0319213 A1 | 11/2017 | Vitali et al. | |
| 2019/0046258 A1 | 2/2019 | Joshi et al. | |
| 2019/0159793 A1 | 5/2019 | Cotter et al. | |
| 2020/0289190 A1 | 9/2020 | Bourgeault et al. | |

FOREIGN PATENT DOCUMENTS

| | | |
|---|---|---|
| EP | 2436329 | 4/2012 |
| EP | 2835108 | 2/2015 |
| EP | 3278747 | 2/2018 |
| EP | 3545892 | 10/2019 |
| WO | 2015183454 A1 | 12/2015 |
| WO | 2020185798 | 9/2020 |

* cited by examiner

INSULATING GRIPS FOR MINIMALLY INVASIVE SURGICAL INSTRUMENTS

CROSS-REFERENCE TO RELATED APPLICATIONS

This application claims the benefit of and priority to U.S. Provisional Application No. 62/961,012, filed on Jan. 14, 2020, which is hereby incorporated by reference.

TECHNICAL FIELD

The present disclosure relates to surgical equipment generally and more specifically to minimally invasive surgical instruments, such as laparoscopic probes, with insulating grips.

BACKGROUND

Minimally invasive surgical techniques can involve inserting instruments into a body cavity through existing openings or small incisions to perform surgical interventions. The surgical instruments used in such techniques may be manipulated remotely, such as via robotic control or human control. For example, in endoscopic or laparoscopic surgeries, an individual may manipulate a surgical instrument within a patient using handles or grips connected to the surgical instrument by control shafts passing into the patient. Thus, surgical interventions can be conducted with less damage to the patient, shorter healing time, and less risk of infection as compared to traditional surgery.

Often, minimally invasive surgical techniques involve the use of electrosurgical instruments. Electrosurgical instruments use the application of electrical currents to perform various surgical tasks, such as cutting, coagulation, desiccation, or fulguration of tissue. Electrical currents can pass through the control shaft and into tissue surrounding the end effector of the surgical instrument.

Many minimally invasive surgical instruments are made to be one-time use instruments. Thus, each instrument is manufactured to be a sterile instrument that, after use, is not intended to be or cannot be re-sterilized, and is discarded.

Some minimally invasive surgical instruments are designed to have a reusable handle to which different shafts can be attached. Each shaft can have a different type of end effector, such as scissors or graspers. End effectors may also be used as electrocautery tools, though this not need be the case for all embodiments. In some cases, the entire shaft can be removed and sterilized. In some cases, the handle can also be sterilized. However, due to the length of the shafts used in various minimally invasive surgeries, these tools can be burdensome to sterilize, such as requiring custom or extra-large sterilization pouches or occupying so much volume in an autoclave that a single set of instruments may need to be autoclaved in multiple batches. As a result, current sterilizable minimally invasive surgical instruments can take a very long time to sterilize and can require the expenditure of multiple batches worth of energy and resources.

Some components of a minimally invasive surgical instrument are made of metal and other components are made of insulating materials. Depending on the component, use of a metal or insulating material may be preferred and in some cases use of one material or the other may be unsuitable. In some cases, metal components contact one another deliberately in the minimally invasive surgical instrument, such as to allow current from an electrical port to be passed to an electrocautery tool. In some cases, metal components that are not intended to receive current may come into contact with other metal components and become electrically charged and inadvertently discharge current to a user or patient when contact with the user or patient is made.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

In an aspect, the present disclosure provides devices, such as minimally invasive surgical devices. An example device of this aspect comprises a handle having an electrical port for receiving a voltage or a current and communicating the voltage or the current to a surgical tip; a first grip mechanically coupled to the handle and having a first internal metal frame and a first insulating overmold over the first internal metal frame, the first internal metal frame comprising a first internal metal portion and a second internal metal portion electrically isolated from the first internal metal portion and mechanically coupled to the first internal metal portion by the first insulating overmold; and a second grip mechanically coupled to the handle and having a second internal metal frame and a second insulating overmold over the second internal metal frame. Optionally, the handle is coupleable to the surgical tip to transfer motion from at least one of the first grip and the second grip to actuate the surgical tip. Optionally, one or more of the first internal metal portion or the second internal metal frame are electrically coupled to the electrical port.

In some examples, the first grip is fixedly coupled to the handle. Optionally, the second grip is movably coupled to the handle. In some examples, the first grip and the handle comprise a unitary structure. Optionally, the handle itself comprises an insulating handle overmold arranged to provide an outer surface electrically insulated from the electrical port.

A ratchet or ratcheting mechanism can be used with the devices of this aspect. For example, a device of this aspect may optionally further comprise a ratchet coupling the first grip and the second grip to limit relative motion between the first grip and the second grip along a direction. Optionally, the ratchet is electrically isolated from the first internal metal portion or the second internal metal frame. Optionally, the ratchet comprises a first ratchet portion coupled to the first grip and a second ratchet portion coupled to the second grip. Optionally, the first ratchet portion and the second ratchet portion slidably engage one another to limit relative motion between the first grip and the second grip along the direction. Optionally, the ratchet further comprises a release for disengaging the first ratchet portion and the second ratchet portion. Optionally, the second ratchet portion is coupled to the second grip by a fastener, such as a fastener that is coupled to the second insulating overmold and electrically isolated from the second internal metal frame. In some examples, the second internal metal frame includes a notch. For example, the second ratchet portion is optionally coupled to the second insulating overmold with a fastener such that the fastener passes through the notch without contacting the second internal metal frame.

As used herein, a notch, also referred to as a cut-out, can correspond to a void, recess, or other structure of an object that is partially surrounded by the main body of the object. A notch, as used herein, is different than a through-hole, in that a notch is not completely surrounded by the body of the object, while a through-hole is completely surrounded by the body of the object. In a grip for a surgical device, a notch can be created within an internal metal frame and coated with another material, such as an insulating overmold, to define a region of a grip that does not have an internal metal frame present therein but which can include the coating material as a primary body of the grip at that location. Such a grip can optionally include an attachment point within the insulating overmold, such as a through-hole, for mechanically coupling other components, such as using a fastener, while limiting contact between the internal metal frame, fastener, or the other components, which could provide electrical coupling between these elements.

Various materials can be used for different elements of the devices of this aspect. For example, the ratchet can optionally comprise a metal, a thermoplastic polymer, or a combination of these. Optionally, one or more of the first internal metal frame, the first internal metal portion, the second internal metal portion, or the second internal metal frame independently comprise steel, stainless steel, surgical stainless steel, aluminum, or titanium. Optionally, one or more of the first insulating overmold or the second insulating overmold independently comprise a thermoplastic polymer, such as polyether ether ketone or polyphenylsulfone.

The insulating materials can prevent metal components of the devices of this aspect from electrically contacting one another or a user or patient. Stated another way, the insulating materials can provide electrical isolation between certain metal components of the device and can provide electrical isolation between metal components and a user or patient. In some examples, one or more of the first insulating overmold or the second insulating overmold can independently exhibit a dielectric strength of from 130 kV/cm to 250 kV/cm. Optionally, one or more of the first insulating overmold or the second insulating overmold is made of an autoclavable and/or sterilizable material.

In another aspect, methods are described herein. An example method of this aspect comprises providing a surgical tip and a handpiece; coupling the surgical tip to the handpiece, the handpiece comprising: a handle having an electrical port for receiving a voltage or a current and communicating the voltage or the current to the surgical tip; a first grip mechanically coupled to the handle and having a first internal metal frame and a first insulating overmold over the first internal metal frame, the first internal metal frame comprising a first internal metal portion and a second internal metal portion electrically isolated from the first internal metal portion and mechanically coupled to the first internal metal portion by the first insulating overmold; and a second grip mechanically coupled to the handle and having a second internal metal frame and a second insulating overmold over the second internal metal frame; decoupling the surgical tip from the handpiece; and autoclaving or sterilizing the handpiece or the surgical tip or both. Optionally, the handle is coupleable to the surgical tip to transfer motion from at least one of the first grip and the second grip to actuate the surgical tip. Optionally, one or more of the first internal metal portion or the second internal metal frame are electrically coupled to the electrical port. Optionally, the surgical tip comprises scissors, graspers, a punch, or a dissector. These or other surgical tips may optionally be used as electrocautery tools. Optionally, the handpiece comprises any of the devices, such as the minimally invasive surgical devices described herein.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
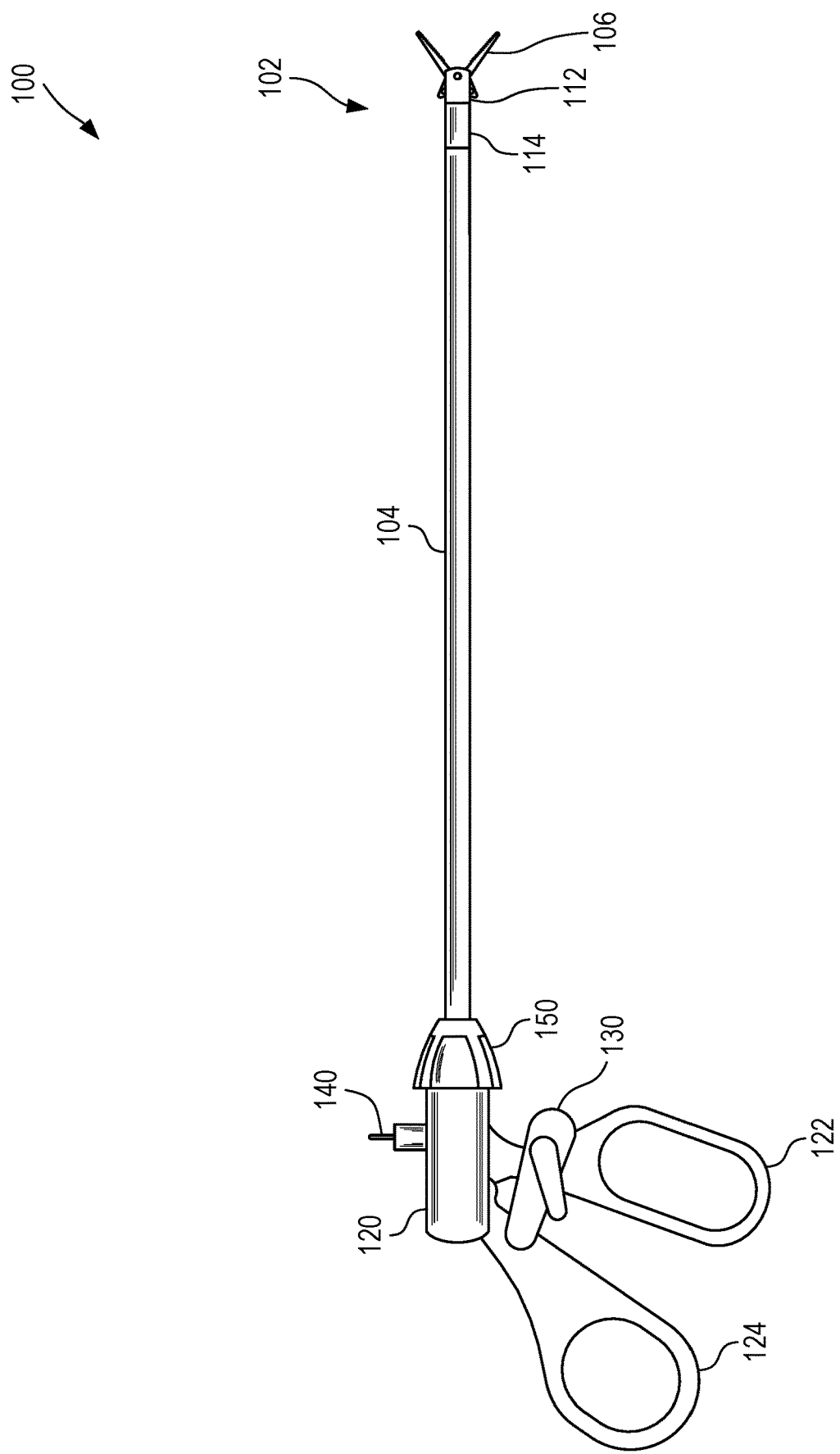
FIG. 1 is a schematic side view depicting a surgical instrument comprising a surgical tip installed on a handpiece according to certain aspects of the present disclosure.

Certain aspects of the present disclosure relate to surgical instruments for minimally invasive surgery. These surgical instruments can be configured for any suitable type of surgery, such as robot-conducted or robot-assisted surgeries, endoscopic surgeries, laparoscopic surgeries, or any other suitable minimally invasive surgery. In some cases, certain aspects of the present disclosure can be especially beneficial for laparoscopic surgical instruments due to the style of surgical instruments used in laparoscopic surgeries. Aspects of the disclosed surgical instruments can comprise metal, which may provide rigidity, strength, and/or electrical conductivity, while other aspects of the disclosed surgical instrument can comprise insulating materials, which may limit the flow of electric current from or to metal components.

A minimally invasive surgical instrument can include a surgical tip removably attachable to a handle via a control shaft. The handle can optionally be non-removably coupled to the control shaft, although that need not always be the case. The combination of a handle and a control shaft, whether the control shaft is removable or not, can be known as a handpiece. The surgical tip is removably couplable to the control shaft, permitting the surgical tip to be cleaned and sanitized on its own. Further, the functionality of the surgical instrument can be quickly changed on the fly, such as mid-surgery, by removing one surgical tip and attaching a different surgical tip. In this fashion, a single handle and control shaft can be used with multiple surgical tips during a surgical procedure, resulting in only a single handle and control shaft set needing to be cleaned and sterilized despite the use of multiple different surgical tips with that same handle and control shaft. As used herein, the surgical instrument can be referred to as having the handle at its proximal end and the surgical tip at its distal end. Thus, the terms distal and proximal as used herein can refer to directions away from and towards the handle-end of the surgical instrument.

Surgical tips can make use of any suitable style of end effector. Suitable styles of end effectors include scissors, graspers, punches, and dissectors. As an example, suitable scissor configurations can include curved scissors, straight scissors, Metzenbaum-style scissors, hooked scissors, or the like. As an example, suitable grasper configurations can include atraumatic graspers, fenestrated graspers, clinching graspers, Babcock-style graspers, Hunter-style graspers, Allis-style graspers, or the like. As an example, suitable punches can include cupped punches, biopsy punches, or the like. As an example, suitable dissectors can include dolphin-nose-style dissectors, Maryland-style dissectors, Birkett grasper-style dissectors, or the like.

End effectors can include one or more movable portions. In some cases, an end effector can move between first and second positions by moving a single movable portion against a stationary portion, such as in a common biopsy punch. In the example of a biopsy punch, a movable portion (e.g., blade) can be forced against a stationary portion (e.g., a biopsy collection surface) to collect a biopsy. This type of action with a single movable portion can be known as single-action, and an end effector using this type of action can be known as a single-action end effector. In some cases, an end effector can have two movable portions, often opposing one another, such as in a common pair of scissors. In the example of scissors, two movable portions (e.g., scissor blades) can be moved towards one another to initiate cutting action. This type of action with two movable portions can be known as dual-action, and an end effector using this type of action can be known as a dual-action end effector. In some cases, however, a scissors may have one fixed blade and one movable blade. Aspects of the present disclosure can be used with single-action or dual-action end effectors. In some cases, aspects of the present disclosure can be used with no-action end effectors having no movable portions (e.g., electrosurgical electrodes).

The handle can include one or more grips for actuating the end effector of the surgical tip through motion of the one or more grips. In some cases, one grip may be locked in place or located at a fixed positioned or fashioned in a unitary construction with the handle, while another grip may have a variable position to actuate the end effector, though that need not always be the case. The handle can be configured in different fashions depending on the desired functionality. Some grips can have ratcheting action while others do not. In some cases, handles can include one or more electrical ports or posts (e.g., cautery posts) to convey electrical voltage and/or current to the control shaft and end effector. Some handles can have short electrical posts while others have long electrical posts. In some cases, a handle can include a flush port to facilitate cleaning of the handle and/or attached control shaft. In some cases, the electrical port can double as a flush port. In some cases, a rotation knob can control rotation of the control shaft, which can in turn control rotation of the end effector of the surgical tip.

In some cases, the various components can be permanently attached to one another, although that need not always be the case. The components can include multiple internal parts that may be movable relative to one another to engage and allow translation of one or more grips to actuate motion of components of the end effector. For example, the control shaft can comprise an outer shaft and an inner shaft. The inner shaft can be moveable within the outer shaft, such as axially movable, to enable actuation of the end effector via manipulation of the inner shaft with respect to the outer shaft. The inner shaft may be mechanically coupled to a variable grip, for example, such that motion of the variable grip is transferred into motion of the inner shaft.

Different components of the surgical instruments can be made of different materials, depending on their position, their likelihood of coming into contact with a patient during surgery, their mechanical requirements, whether they need to be electrically conductive or electrically insulating, or the like. For reusability, it is desirable to make components of the surgical instruments from materials that can withstand sterilization procedures, such as pressures, temperatures, and conditions generated within an autoclave. Example materials compatible with sterilization procedures include, but are not limited to, metals and thermoplastic polymers, such as polyether ether ketone (PEEK) or polyetherimide (PEI) or polyphenylsulfone.

The structure and materials used in the surgical devices may be used to limit or control the electrical conductivity between various components and to enhance reliability and safety. For example, components, such as the handle, can comprise a metal coated in an electrically insulating material, such as PEEK or PEI. In some cases, the components can comprise the electrically insulating material directly, with embedded metal or other structures to allow for interfacing with other components, such as an electrical port or flush port, a control shaft, grips, or the like. As another example, the outer shaft can be made of or coated in an electrically insulating material, such as PEEK or PEI. The inner shaft can be made of an electrically conductive material, such as a metal. In some cases, the inner shaft can be made of the same material as elements or components of the surgical tip.

In some cases, the components of the surgical instruments may benefit from the structural rigidity, material strength, and wear resistance provided by a metal. However, since metal components are electrically conductive, it can be beneficial to coat them, at least partially, with an electrically insulating material if limiting exposure of electrically conductive surfaces is useful. In some cases, however, it may be impractical or undesirable to fabricate certain components using insulating materials.

In some examples, a ratchet may include a gear or a rack having one or more teeth and a spring-loaded pawl that engages a depression between or behind the teeth, enabling facile motion along one direction and preventing motion along the reverse direction. The ratchet can include a release or otherwise be movable to allow the pawl and teeth to disengage to reset or adjust the position in both the forward and reverse directions. Optionally, the ratchet can automatically engage the release or disengage the pawl and the teeth at the maximum relative travel positions of the grips. The teeth, pawl, and release can optionally be made of metal, such as steel, for enhanced strength and reliability, though this need not be the case. Optionally, the one or more teeth and a pawl can be made of a metal since these components move relative to one another and may experience wear or be subject to stresses for which non-metallic components, such as insulating materials like PEEK, may not be suitable.

In some cases, components of a surgical device may come into contact with a user or patient during a surgical procedure, potentially exposing the user or patient to an electrically conductive surface in an undesirable way. It may, therefore, be beneficial to control whether and to what extent the components can come into contact with other electrically conductive structures. As an example, a structure of the grips of a surgical instruments can be arranged to limit the electrical conductivity between various components and to enhance safety. For example, the grips can comprise or include an electrically insulating material, such as PEEK, optionally coated over an internal frame, which can comprise or include metal portions. In some cases, metal is included as a frame of a grip for strength and rigidity and optionally to engage or mechanically couple to the handle, a control shaft, and/or a ratchet, which can optionally be made of metal.

The internal frame of the grips can be made of multiple metal portions that are spaced apart from one another to disconnect the electrical pathway between the metal portions. Insulating materials can be used to mechanically couple the multiple portions together to while still providing electrical isolation between the portions. For example, two internal metal portions of an internal frame of a grip can be overmolded with an insulating material to mechanically couple the internal metal portions and provide electrical isolation between them.

In some cases, positions of an internal metal frame of a grip where a pin or other fastener mechanically couples another component to the grip, such as a ratchet, may include a notch or cutout that is overmolded with an insulating material, such that the pin or other fastener mechanically couples to the insulating material only and cannot come into contact with an internal metal frame.

Example insulating materials comprise thermoplastic polymers, such as polyether ether ketone (PEEK) or polyphenylsulfone. Such polymers can enable the grips to resist damage from inadvertent contact with other tools and surfaces and these polymers are also capable of withstanding sterilization procedures. In cases where the surgical device is only a single use device, the insulating material may not have to withstand sterilization procedures and so other materials, such as an acetal, a polypropylene, a polycarbonate, a polyethylene, a polyvinylidene fluoride, a polyester, or other medical grade plastics, may be employed.

The insulating material can have a sufficiently high dielectric strength. In some cases, the dielectric strength of the insulating can be at or greater than approximately 230 kV/cm, such as at or greater than approximately 130 kV/cm, 135 kV/cm, 140 kV/cm, 145 kV/cm, 150 kV/cm, 155 kV/cm, 160 kV/cm, 165 kV/cm, 170 kV/cm, 175 kV/cm, 180 kV/cm, 185 kV/cm, 190 kV/cm, 195 kV/cm, 200 kV/cm, 205 kV/cm, 210 kV/cm, 215 kV/cm, 220 kV/cm, 225 kV/cm, 230 kV/cm, 235 kV/cm, 240 kV/cm, 245 kV/cm, and/or 250 kV/cm.

Useful insulating material include those comprising a thermoplastic polymer that is suitable for use in surgical tools and is sterilizable and/or autoclavable. Useful insulating materials include those having a glass transition temperature that is from 121° C. to 300° C. (e.g., at or above 140° C., 143° C., or 288° C.). In some cases, the insulating material can have a melting temperature that is from 300° C. to 350° C. (e.g., at or above 340° C. or 343° C.). The sufficiently high glass transition temperature and/or melting temperature can ensure the insulating material does not lose shape or integrity when subjected to sterilization procedures in an autoclave, which can reach temperatures of up to 121° C. (e.g., for gravity-based sterilizers) or 135° C. (e.g., for vacuum-based sterilizers). In some cases, the insulating material can have a glass transition temperature above a maximum temperature of a sterilization procedure for sterilizing the surgical tip. Such a sterilization procedure can be a sterilization procedure shared with other equipment commonly used with the surgical tip, such as a scalpel used to create an incision into which the surgical tip can be maneuvered.

Aspects and features of the present disclosure enable minimally invasive surgical equipment that is easy and efficient to store, is safe and easy to use, has well-insulated surgical tips, handles, and other portions, can be easily and efficiently sterilized, and is highly customizable.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic side view depicting a minimally invasive surgical instrument 100 comprising a surgical tip 102 installed on a control shaft 104 coupled to a handle 120 according to certain aspects of the present disclosure. The surgical tip 102 is removably coupled to the control shaft 104. In some cases, the control shaft 104 can be removably coupled to the handle 120, although that need not be the case. In some cases, the control shaft 104 is permanently coupled to the handle 120.

The surgical tip 102 can include a multi-part hub comprising a distal hub 112 and a proximal hub 114. The surgical tip 102 can be removably coupled to the control shaft 104 via proximal hub 114, which is in turn permanently coupled to distal hub 112, which is movably secured to the end effector 106. Proximal hub 114 can optionally include one or more sets of threads to allow for strong yet removable mechanical coupling between proximal hub 114 and corresponding threads on control shaft 104. Additional details of coupling of surgical tip 102 and actuation of end effector 106 can be found, for example, in U.S. patent application Ser. No. 16/298,817, filed on Mar. 11, 2019, which is hereby incorporated by reference in its entirety.

The handle 120 is attached to a fixed grip 122 and a variable grip 144 for manipulating the end effector 106 of the surgical tip 102. Movement of the variable grip 124 can cause the inner shaft of the control shaft 104 to move axially with respect to the outer shaft, thus causing the end effector to actuate (e.g., move between first and second positions), optionally via mechanical coupling to one or more intervening elements. In some cases, manipulation of the variable grip 124 can be further controlled by a ratcheting mechanism 130, although that need not always be the case. Ratcheting mechanism 130 can be external to handle 120, though that need not always be the case and ratcheting mechanism 130 can optionally be internal to handle 120. In some cases, handle 120 can include a rotary knob 150. Rotary knob 150 can be manipulated to control rotation of the control shaft 104, thus controlling rotation of the surgical tip 102.

In some cases, the handle 120 can include a port 140. Port 140 can act as one or both of an electrical port and a flush port. When used as an electrical port, port 140 can convey electrical current to the inner shaft of the control shaft 104, which can in turn convey the electrical current through to the end effector 106 of the surgical tip 302, optionally via electrical coupling to one or more intervening elements. This electrical current can be used for various electrosurgical techniques, including cauterizing. When used as a flush port, port 140 can permit fluid to be flushed through the control shaft 104, such as to facilitate cleaning and/or sterilization of the control shaft 104. In some cases, such as when the control shaft 104 is permanently coupled to the handle 120, the use of a flush port can be especially useful. In some cases, handle 120 can include any number of ports 140, each of which can act as one or more of an electrical port and a flush port.

Figure 2A:
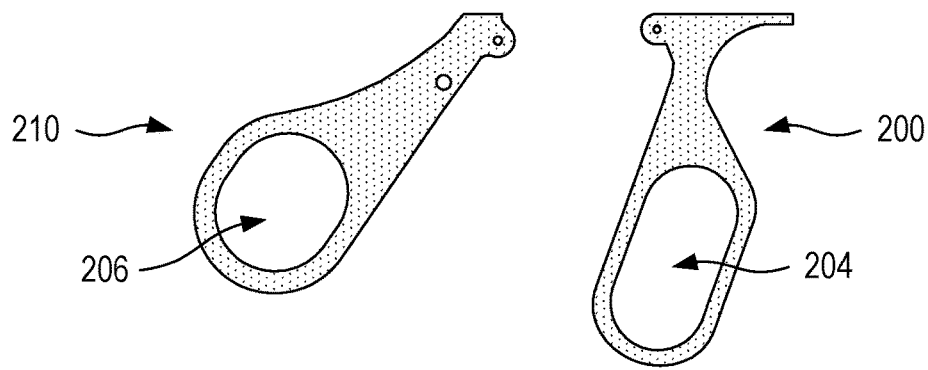
FIG. 2A is a schematic side view of grips of a surgical instrument showing an insulating overmold according to certain aspects of the present disclosure.
Figure 2B:
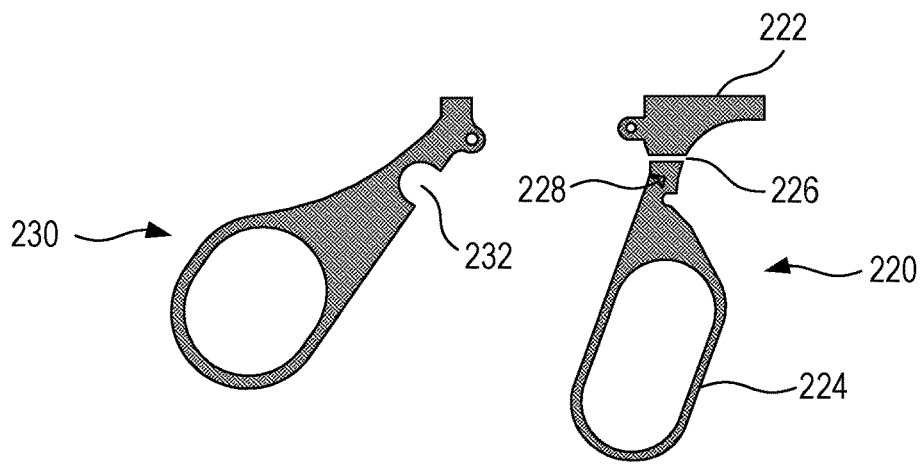
FIG. 2B is a schematic side view of grips of a surgical instrument showing an internal metal frame according to certain aspects of the present disclosure.
Figure 2C:
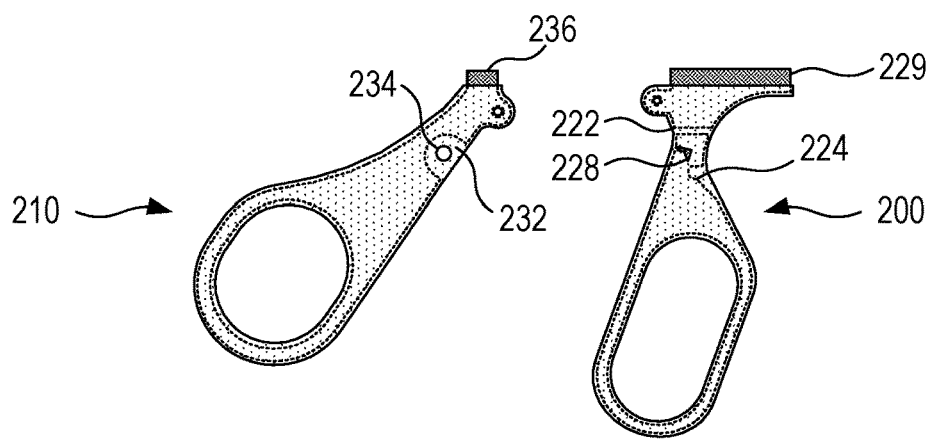
FIG. 2C is a schematic side view of grips of a surgical instrument showing the position of an internal metal frame within an insulating overmold according to certain aspects of the present disclosure.

FIGS. 2A-2C are a set of schematic side views depicting grips of a surgical instrument. In FIG. 2A, grips 200 and 210 are depicted, representing a first and second grip of a surgical instrument, such as minimally invasive surgical instrument 100 depicted in FIG. 1. Grips 200 and 210 may optionally correspond to grips 122 and 124, respectively of FIG. 1. Grip 200 may correspond to a fixed grip, meaning it is or can be coupled to a handle of a surgical instrument in a way that the grip 200 does not move relative to the handle. Grip 210 may correspond to a variable grip, meaning it is can be coupled to a handle of a surgical instrument in a way that the grip 200 does can move relative to the handle. Alternatively, grip 200 can be a variable grip, grip 210 can be a fixed grip, or both grips 200 and 210 can be variable grips. Grips 200 and 202 may include openings 204 and 206, respectively, providing a location for a user to insert a finger and/or grasp grips 200 and 202 during use. Optionally, grips 200 and 202 may not include any openings for a user's fingers. In FIG. 2A, an insulating overmold is schematically depicted as coated over surfaces of grips 200 and 210.

FIG. 2B schematically depicts internal metal frames 220 and 230, corresponding to an internal metal structure of grips 200 and 210, respectively. FIG. 2C schematically depicts a position of internal metal frames 220 and 230 within an insulating overmold of grips 200 and 210.

Internal metal frames 220 and 230 can have shapes that do not exactly match those of grips 200 and 210, however, and can include additional features different from those of grips 200 and 210. For example, internal metal frame 220 is constructed from multiple internal metal portions, such as internal metal portion 222 and internal metal portion 224, separated by a gap 226, which can provide electrical isolation between internal metal portion 222 and internal metal portion 224. These separate internal metal portions 222 and 224 can be mechanically coupled to one another via the insulating overmold that fills in gap 226 and coats internal metal portions 222 and 224 with a unitary coating. Additionally, internal metal frame 220 can include a tooth 228, which may extend above a surface of internal metal portion 224 and be used to engage or as part of a ratcheting mechanism to limit translation of grip 200 or 210 during use. Tooth 228 may or may not be coated by the insulating overmold, depending on the particular construction of grip 200. Additionally, internal metal frame 220 can optionally include a region 229 that extends beyond the extent of the insulating overmold, such as for mechanically coupling internal metal frame 220 to other elements, such as a handle of a surgical device.

As another example, internal metal frame 230 can include a cutout, recess, notch or other feature 232 corresponding to a region of internal metal frame 230 where metal material is not present but which is overmolded with an insulating material, as depicted in FIG. 2C. An opening 234 may be present within the insulating overmold at the location of feature 232, which can be used to attach a pin or other fastener to allow another component to attach to grip 210, such as a ratchet mechanism or portion thereof, without making electrical contact with internal metal frame 230. Additionally, internal metal frame 230 can optionally include a region 236 that extends beyond the extent of the insulating overmold, such as for mechanically coupling internal metal frame 230 to other elements, such as a handle of a surgical device or a control shaft or component thereof.

Figure 3:
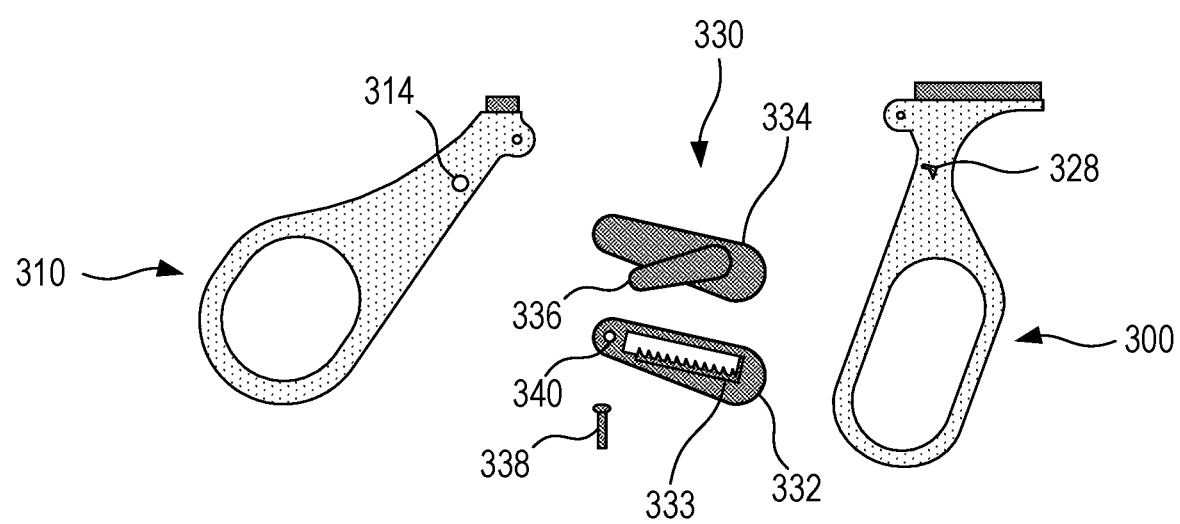
FIG. 3 is a schematic side view depicting a grips of a surgical instrument and an expanded schematic view of an example ratchet according to certain aspects of the present disclosure.

FIG. 3 provides side schematic illustration of grips 300 and 310 and an exploded ratchet 330. Ratchet 330 may optionally correspond, for example, to ratcheting mechanism 130 depicted in FIG. 1. Grips 300 and 310 may optionally correspond, for example, to grips 200 and 210, respectively, depicted in FIGS. 2A and 2C and may optionally include internal metal frames 220 and 230, respectively, depicted in FIG. 2B. Ratchet 330 may include multiple components, such as bottom 332, including pawl 333, and cover 334. Tooth 328 may pass into bottom 332 and engage pawl 333 to limit an amount and/or direction of relative translation between grips 300 and 310. By using an internal metal frame in grip 300 that includes multiple internal metal portions electrically isolated from one another, as with internal metal frame 220 depicted in FIG. 2B, tooth 328 can be electrically isolated from components of a surgical device handle, and so pawl 333 can also be electrically isolated from the from components of the surgical device handle, despite contact with tooth 328.

Cover 334 may include a release 336, allowing for pawl 333 and tooth 328 to disengage from one another to allow for relative translation between grips 300 and 310 to be at least partially unrestricted. A pin 338 or other fastener can be used to attach ratchet 330 to grip 310, such as by passing through opening 314 in grip 310 and opening 340 in bottom 332 while being fixed to cover 334. Attaching ratchet 330 to grip 310 at opening 314 can allow ratchet 330 to be mechanically coupled to grip 310 and yet remain electrically isolated from an internal metal frame within grip 310 if opening 314 is positioned at a notch, recess, cutout or other region within grip 310 where the internal metal frame is not present. Such a configuration can further allow ratchet 330 to be electrically isolated from components of a surgical device handle even if the internal metal frame is electrically connected to the components of the surgical device handle.

The way of attaching ratchet 330 to grips 300 and 310 described above and depicted in FIG. 3 is merely one example and it will be appreciated that other configurations may be used. In some cases, ratchet 330 can be removably attached to grip 310 to permit ratchet 330 to be replaced if it has worn out.

Figure 4:
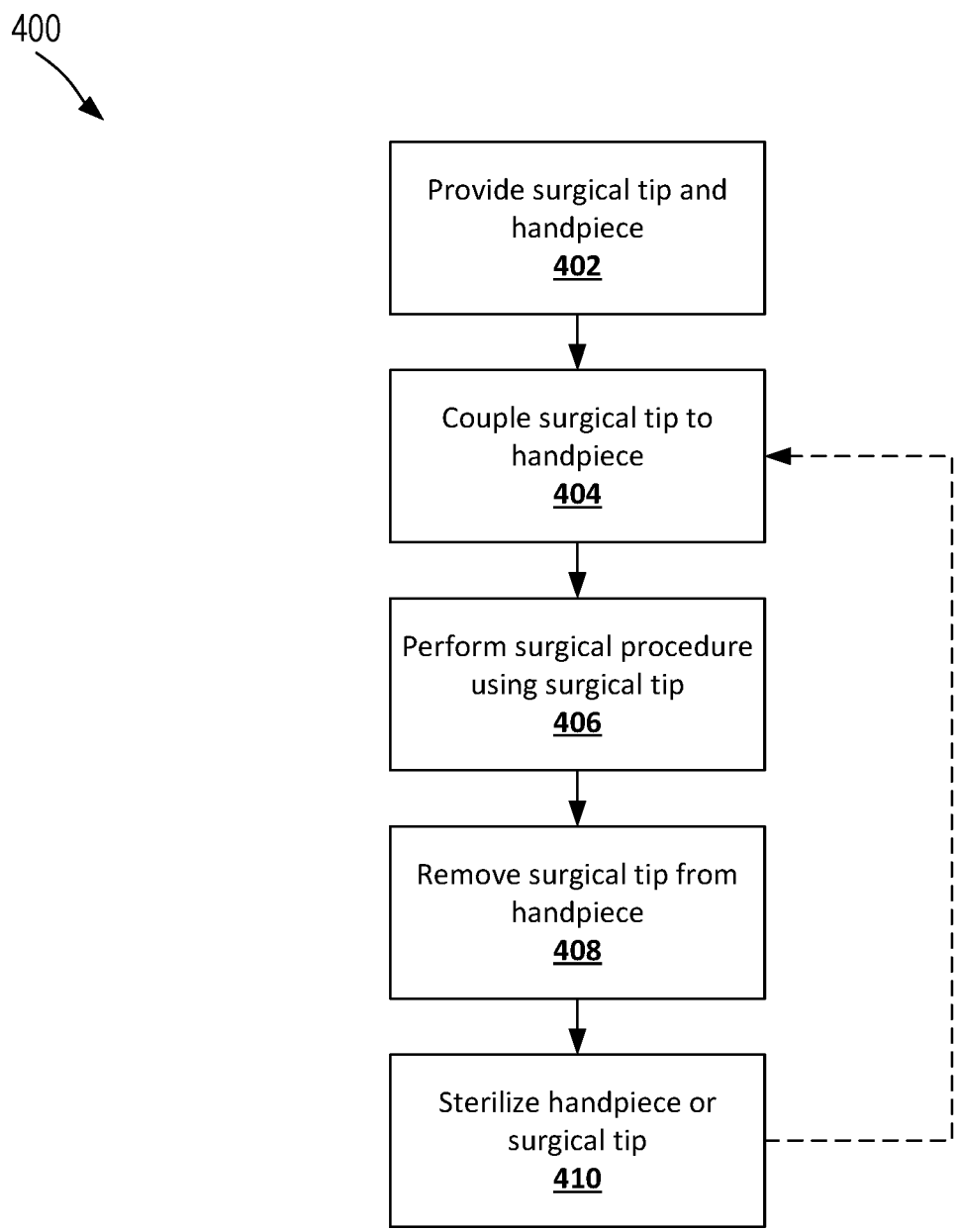
FIG. 4 is a flowchart providing an overview of a process for using a surgical instrument according to certain aspects of the present disclosure.

FIG. 4 is a flowchart depicting a process 400 for using a surgical instrument according to certain aspects of the present disclosure. At block 402, a surgical tip and handpiece can be provided. The surgical tip can be any suitable surgical tip, such as surgical tip 102 of FIG. 1. The handpiece can be any suitable handpiece, such as comprising handle 120 and control shaft 104 of FIG. 1. The surgical tip and handpiece can be in a sterilized condition, suitable for use in a surgical procedure. In some cases, the surgical tip can be provided from a kit of multiple surgical tips, each having a different end effector. In some cases, providing a surgical tip can include providing a sterilized surgical tip in a sterilizing pouch.

At block 404, the surgical tip can be coupled to the handpiece. The handpiece can include a control shaft coupled (e.g., permanently or removably) to a handle. The surgical tip can be removably coupled to the handpiece. In some cases, coupling the surgical tip to the handpiece can include screwing a yoke of the surgical tip to an inner shaft of the handpiece. In some cases, coupling the surgical tip to the handpiece can include screwing a proximal hub of the surgical tip to an outer shaft of the handpiece. In some cases, coupling the surgical tip to the handpiece can include screwing a yoke of the surgical tip to an inner shaft of the handpiece and screwing a proximal hub of the surgical tip to an outer shaft of the handpiece.

At block 406, a surgical procedure can be performed using the surgical tip. In some cases, performing a surgical procedure can include passing an electrical current through tissue adjacent the surgical tip using the surgical tip. In some cases, passing electrical current through tissue adjacent the surgical tip can include passing electrical current through targeted tissue adjacent an end effector of the surgical tip and not applying electrical current to non-targeted tissue adjacent the proximal hub of the surgical tip. In some cases, performing a surgical procedure can include actuating an end effector of the surgical tip within a patient by translating one or more grips of or connected to the handpiece. In some cases, performing a surgical procedure can include actuating an end effector of the surgical tip to close one or more movable portions of the end effectors around tissue. In some cases, performing a surgical procedure can include actuating a ratchet to restrict or translation of one or more grips of or connected to the handpiece. In some cases, performing a surgical procedure can include releasing a ratchet to enable translation of one or more grips of or connected to the handpiece.

At block 408, the surgical tip can be removed from the handpiece. Removing the surgical tip from the handpiece can be the opposite of coupling the surgical tip to the handpiece from block 404, such as unscrewing the surgical tip from the handpiece.

At block 410, the surgical tip or the handpiece, or both, can be sterilized. In some cases, sterilizing the surgical tip or handpiece can include cleaning and sterilizing the surgical tip or handpiece. In some cases, sterilizing the surgical tip or handpiece can include autoclaving the surgical tip or handpiece. In some cases, sterilizing the surgical tip or handpiece can include subjecting the surgical tip or handpiece to temperatures at or above 121° C. or 135° C. In some cases, sterilizing the surgical tip or handpiece can include placing the surgical tip or handpiece in a sterilizing pouch.

After being sterilized, the surgical tip or handpiece can be reused, such as by coupled to one another or to another surgical tip or handpiece a handpiece. Coupling the surgical tip to the handpiece can occur at a repeated block 404 as part of an additional surgical operation distinct from the surgical operation associated with the surgical procedure described above. For example, the first surgical procedure from can be performed on a first patient and a repeated surgical procedure be associated with a surgical procedure to be performed on a second patient.

In some cases, after block 410, if the surgical tip or handpiece are deemed to have undergone too many use-and-sterilization cycles (e.g., blocks 404, 406, 408, 410) such that the surgical tip or the handpiece are no longer acceptable for use, one or both the surgical tip or the handpiece can be disposed of or refurbished.

As used below, any reference to a series of examples is to be understood as a reference to each of those examples disjunctively (e.g., "Examples 1-4" is to be understood as "Examples 1, 2, 3, or 4").

Example 1 is a device comprising: a handle having an electrical port for receiving a voltage or a current and communicating the voltage or the current to a surgical tip; a first grip mechanically coupled to the handle and comprising or consisting of a first internal metal frame and a first insulating overmold over the first internal metal frame, the first internal metal frame comprising or consisting of a first internal metal portion and a second internal metal portion electrically isolated from the first internal metal portion and mechanically coupled to the first internal metal portion by the first insulating overmold; and a second grip mechanically coupled to the handle and having a second internal metal frame and a second insulating overmold over the second internal metal frame; wherein the handle is coupleable to the surgical tip to transfer motion from at least one of the first grip and the second grip to actuate the surgical tip, and wherein one or more of the first internal metal portion or the second internal metal frame are electrically coupled to the electrical port.

Example 2 is the device of example 1, wherein the first grip is fixedly coupled to the handle and wherein the second grip is movably coupled to the handle.

Example 3 is the device of example 2, wherein the first grip and the handle comprise a unitary structure.

Example 4 is the device of examples 1-3, wherein the handle comprises an insulating handle overmold arranged to provide an outer surface electrically insulated from the electrical port.

Example 5 is the device of examples 1-4, further comprising a ratchet coupling the first grip and the second grip to limit relative motion between the first grip and the second grip along a direction.

Example 6 is the device of example 5, wherein the ratchet is electrically isolated from the first internal metal portion or the second internal metal frame.

Example 7 is the device of examples 5-6, wherein the ratchet comprises a first ratchet portion coupled to the first grip and a second ratchet portion coupled to the second grip, wherein the first ratchet portion and the second ratchet portion slidably engage one another to limit relative motion between the first grip and the second grip along the direction.

Example 8 is the device of example 7, wherein the second ratchet portion is coupled to the second grip by a fastener, wherein the fastener is coupled to the second insulating overmold and electrically isolated from the second internal metal frame.

Example 9 is the device of examples 7-8, wherein the second internal metal frame includes a notch, wherein the second ratchet portion is coupled to the second insulating overmold with a fastener such that the fastener passes through the notch without contacting the second internal metal frame.

Example 10 is the device of examples 7-9, wherein the ratchet further comprises a release for disengaging the first ratchet portion and the second ratchet portion.

Example 11 is the device of examples 5-10, wherein the ratchet comprises a metal, a thermoplastic polymer, or a combination of these.

Example 12 is the device of examples 1-11, wherein one or more of the first internal metal frame, the first internal metal portion, the second internal metal portion, or the second internal metal frame independently comprise steel, stainless steel, surgical stainless steel, aluminum, or titanium.

Example 13 is the device of examples 1-12, wherein one or more of the first insulating overmold or the second insulating overmold independently comprise a thermoplastic polymer, polyether ether ketone, or polyphenylsulfone.

Example 14 is the device of examples 1-13, wherein one or more of the first insulating overmold or the second insulating overmold independently exhibit a dielectric strength of from 130 kV/cm to 250 kV/cm.

Example 15 is the device of examples 1-14, wherein one or more of the first insulating overmold or the second insulating overmold is made of an autoclavable and/or sterilizable material.

Example 16 is the device of examples 1-15, further comprising a control shaft coupled to the handle.

Example 17 is the surgical device of example 16, wherein the control shaft is removably coupled to the handle.

Example 18 is the device of examples 16-17, wherein the surgical tip is removably coupled to the control shaft.

Example 19 is a method, comprising: providing a surgical tip and a handpiece; coupling the surgical tip to the handpiece, the handpiece comprising: a handle having an electrical port for receiving a voltage or a current and communicating the voltage or the current to the surgical tip; a first grip mechanically coupled to the handle and having a first internal metal frame and a first insulating overmold over the first internal metal frame, the first internal metal frame comprising a first internal metal portion and a second internal metal portion electrically isolated from the first internal metal portion and mechanically coupled to the first internal metal portion by the first insulating overmold; and a second grip mechanically coupled to the handle and having a second internal metal frame and a second insulating overmold over the second internal metal frame; wherein the handle is coupleable to the surgical tip to transfer motion from at least one of the first grip and the second grip to actuate the surgical tip, and wherein one or more of the first internal metal portion or the second internal metal frame are electrically coupled to the electrical port; decoupling the surgical tip from the handpiece; and autoclaving the handpiece.

Example 20 is the method of example 19, wherein the surgical tip comprises an electrocautery tool, scissors, graspers, a punch, and/or dissectors.

Example 21 is the method of examples 19-20, wherein the handpiece comprises the device of any of examples 1-18.

The foregoing description of the embodiments and examples, including illustrated embodiments and examples, has been presented only for the purpose of illustration and description and is not intended to be exhaustive or limiting to the precise forms disclosed. Numerous modifications, adaptations, and uses thereof will be apparent to those skilled in the art.

What is claimed is:

1. A device comprising:
 a handle having an electrical port for receiving a voltage or a current and communicating the voltage or the current to a surgical tip;
 a first grip mechanically coupled to the handle and having a first internal metal frame and a first insulating overmold over the first internal metal frame, the first internal metal frame comprising a first internal metal portion and a second internal metal portion electrically isolated from the first internal metal portion and mechanically coupled to the first internal metal portion by the first insulating overmold; and
 a second grip mechanically coupled to the handle and having a second internal metal frame and a second insulating overmold over the second internal metal frame,
 wherein the handle is coupleable to the surgical tip to transfer motion from at least one of the first grip and the second grip to actuate the surgical tip, and wherein one or more of the first internal metal portion or the second internal metal frame are electrically coupled to the electrical port.

2. The device of claim 1, wherein the first grip is fixedly coupled to the handle and wherein the second grip is movably coupled to the handle.

3. The device of claim 2, wherein the first grip and the handle comprise a unitary structure.

4. The device of claim 1, wherein the handle comprises an insulating handle overmold arranged to provide an outer surface electrically insulated from the electrical port.

5. The device of claim 1, further comprising a ratchet coupling the first grip and the second grip to limit relative motion between the first grip and the second grip along a direction.

6. The device of claim 5, wherein the ratchet is electrically isolated from the first internal metal portion or the second internal metal frame.

7. The device of claim 5, wherein the ratchet comprises a first ratchet portion coupled to the first grip and a second ratchet portion coupled to the second grip, wherein the first ratchet portion and the second ratchet portion slidably engage one another to limit relative motion between the first grip and the second grip along the direction.

8. The device of claim 7, wherein the second ratchet portion is coupled to the second grip by a fastener, wherein the fastener is coupled to the second insulating overmold and electrically isolated from the second internal metal frame.

9. The device of claim 7, wherein the second internal metal frame includes a notch, wherein the second ratchet portion is coupled to the second insulating overmold with a fastener such that the fastener passes through the notch without contacting the second internal metal frame.

10. The device of claim 7, wherein the ratchet further comprises a release for disengaging the first ratchet portion and the second ratchet portion.

11. The device of claim 5, wherein the ratchet comprises a metal, a thermoplastic polymer, or a combination of these.

12. The device of claim 1, wherein one or more of the first internal metal frame, the first internal metal portion, the second internal metal portion, or the second internal metal frame independently comprise steel, stainless steel, surgical stainless steel, titanium, or aluminum.

13. The device of claim 1, wherein one or more of the first insulating overmold or the second insulating overmold independently comprise a thermoplastic polymer, polyether ether ketone, or polyphenylsulfone.

14. The device of claim 1, wherein one or more of the first insulating overmold or the second insulating overmold independently exhibit a dielectric strength of from 130 kV/cm to 250 kV/cm.

15. The device of claim 1, wherein one or more of the first insulating overmold or the second insulating overmold is made of an autoclavable or sterilizable material.

16. The device of claim 1, further comprising a control shaft coupled to the handle.

17. The device of claim 16, wherein the control shaft is removably coupled to the handle.

18. The device of claim 16, wherein the surgical tip is removably coupled to the control shaft.

19. A method, comprising:
 providing a surgical tip and a handpiece;
 coupling the surgical tip to the handpiece, the handpiece comprising:

a handle having an electrical port for receiving a voltage or a current and communicating the voltage or the current to the surgical tip;

a first grip mechanically coupled to the handle and having a first internal metal frame and a first insulating overmold over the first internal metal frame, the first internal metal frame comprising a first internal metal portion and a second internal metal portion electrically isolated from the first internal metal portion and mechanically coupled to the first internal metal portion by the first insulating overmold; and a second grip mechanically coupled to the handle and having a second internal metal frame and a second insulating overmold over the second internal metal frame;

wherein the handle is coupleable to the surgical tip to transfer motion from at least one of the first grip and the second grip to actuate the surgical tip, and wherein one or more of the first internal metal portion or the second internal metal frame are electrically coupled to the electrical port;

decoupling the surgical tip from the handpiece; and autoclaving the handpiece.

20. The method of claim 19, wherein the surgical tip comprises an electrocautery tool, scissors, graspers, a punch, or dissectors.

\* \* \* \* \*